(12) United States Patent
Koch et al.

(10) Patent No.: US 6,562,003 B2
(45) Date of Patent: May 13, 2003

(54) SAFELY DISPOSABLE HYPODERMIC SYRINGE

(75) Inventors: Johan Koch, Saltsjöbaden (SE); Joakim Jemseby, Danderyd (SE)

(73) Assignee: JK Medicinkonsult Förvaltning AB (SE)

( * ) Notice: Subject to any disclaimer, the term of this patent is extended or adjusted under 35 U.S.C. 154(b) by 0 days.

(21) Appl. No.: 09/800,833

(22) Filed: Mar. 7, 2001

(65) Prior Publication Data

US 2002/0128609 A1 Sep. 12, 2002

(51) Int. Cl.$^7$ .................................................. A61M 5/00
(52) U.S. Cl. ........................ 604/110; 604/198; 604/218
(58) Field of Search .................... 604/110, 195, 604/263, 198, 192, 187, 218

(56) References Cited

U.S. PATENT DOCUMENTS

| | | | |
|---|---|---|---|
| 3,356,089 A | 12/1967 | Francis | 128/221 |
| 3,487,834 A | 1/1970 | Smith, Jr. et al. | 128/218 |
| 4,692,156 A | 9/1987 | Haller | 604/195 |
| 5,222,945 A * | 6/1993 | Basnight | 604/110 |
| 5,267,976 A | 12/1993 | Guerineau | 604/198 |
| 5,376,080 A * | 12/1994 | Petrussa | 604/198 |
| 5,554,122 A * | 9/1996 | Emanuel | 604/110 |
| 5,855,839 A | 1/1999 | Brunel | 264/524 |
| 5,997,511 A | 12/1999 | Curie et al. | 604/195 |
| 6,206,853 B1 * | 3/2001 | Bonnet | 604/110 |
| 6,224,575 B1 * | 5/2001 | Garvin | 604/195 |
| 6,241,707 B1 * | 6/2001 | Dysarz | 604/110 |
| 6,248,094 B1 * | 6/2001 | Epperson | 604/195 |
| 6,419,658 B1 * | 7/2002 | Restelli et al. | 604/110 |

FOREIGN PATENT DOCUMENTS

| | | | |
|---|---|---|---|
| EP | 0581523 | 2/1994 | |
| FR | 2650187 | 2/1991 | 5/50 |
| FR | 2727021 | 5/1996 | 5/50 |
| WO | 9013325 | 11/1990 | 5/50 |
| WO | 0180931 | 11/2001 | 5/32 |

OTHER PUBLICATIONS

International Search Report No. PCT/SE02/00397 dated Jun. 13, 2002.

* cited by examiner

*Primary Examiner*—Sharon Kennedy
(74) *Attorney, Agent, or Firm*—Ostrolenk, Faber, Gerb & Soffen, LLP (57) ABSTRACT

A disposable hypodermic syringe comprises an outer barrel, an inner barrel slidingly disposable in the outer barrel, a hypodermic needle disposed axially at the front end of the outer barrel so as penetrate its front end wall and being held, at its rear end, by the front end wall of the inner barrel, and a plunger which is slidingly disposable in the inner barrel. The outer barrel includes elements for interlocking with the inner barrel when the inner barrel is in a fully inserted position. The plunger includes release elements for releasing the inner barrel from the outer barrel while interlocking with the inner barrel so as to allow the inner barrel and the plunger to be withdrawn in combination with the hypodermic needle for a distance sufficient to displace the needle into a space formed between the outer barrel and the inner barrel.

18 Claims, 10 Drawing Sheets

SAFELY DISPOSABLE HYPODERMIC SYRINGE

FIELD OF THE INVENTION

The present invention relates to a hypodermic syringe which cannot be re-used and which is safely disposable.

BACKGROUND OF THE INVENTION

The re-use of hypodermic syringes by drug abusers is a recognized health problem. Accidental injury of health care personnel and others by used and discarded hypodermic, potentially contaminated syringes, also is an important health problem. A great number of hypodermic syringes of the aforementioned kind have been proposed over the last decades. While a number of them seem to solve the technical problems involved in providing a safely disposable singe-use hypodermic syringe, their design might be considerably improved in regard of economy of construction and safety of function.

OBJECTS OF THE INVENTION

One object of the present invention is to provide a hypodermic syringe which can be safely disposed and which cannot be used after a single injection.

Another object of the present invention is to provide a hypodermic syringe of the aforementioned kind consisting of as few parts as possible, and which is easily manufactured.

Still another object of the invention is to provide a hypodermic syringe of the aforementioned kind having a negligible dead space.

An additional object of the present invention is to provide a hypodermic syringe of the aforementioned kind in which the bond between the needle and the syringe is not easily accidentally broken and which is resistant to leakage.

Further objects of the present invention will become obvious from the following brief description of the invention, a drawing illustrating a preferred embodiment thereof described in more detail, and the appended claims.

BRIEF DESCRIPTION OF THE INVENTION

The present invention concerns a disposable hypodermic syringe, comprising:
- an outer barrel having a front end wall and an open rear end,
- an inner barrel having a front end wall and an open rear end, slidingly disposable in the outer barrel,
- a hypodermic needle disposed axially at the front end of the outer barrel so as penetrate its front end wall and being held, at the rear end of the needle, by the front end wall of the inner barrel,
- a plunger slidingly disposable in the inner barrel.

The outer barrel comprises means for interlocking with the inner barrel when the latter is in a fully inserted position. The plunger comprises means for releasing the inner barrel from the outer barrel while the plunger interlocks with the inner barrel so as to allow the plunger and the inner barrel to be withdrawn in combination with the hypodermic needle for a distance sufficient to displace the needle into a space formed between the outer barrel and the inner barrel.

In this specification, the terms "front", "rear", "forward", "rearward", "distal", "proximal", etc. retain their conventional meanings. The front (distal) end of the syringe is the end provided with the needle, the rear (proximal) end is the end provided with the plunger.

The bodies of the outer and inner barrel are substantially cylindrical and fit snugly over their entire facing areas. The inner barrel and the outer barrel are made of a polymer material which is somewhat flexible, such as polypropylene.

According to a first preferred aspect of the invention the means for locking the inner barrel to the outer barrel comprise a circumferential slit in the wall of the inner barrel disposed near its rear end and a projection extending in a radial direction inward from the inner wall of the outer barrel so as to be located in the slit. It is preferred for the projection to be disposed at a wall section that is flanked by axially extending slits so as to make the projection easily deflectable in an outward radial direction. Its deflection may be further supported by a cut-out disposed distally of the projection.

According to a second preferred aspect of the invention the means at the plunger for releasing the inner barrel from the outer barrel comprises a finger extending radially from a radial flange of the plunger. The finger is insertable into the slit of the inner barrel is and displaceable in the slit so as to expel the projection. of the outer barrel. The slit is preferably open-ended at one end for insertion of the plunger finger. It is preferred that the finger insertion is by a distal displacement of the plunger. Thus the insertion portion of the slit extends in an axial direction while the remainder of the slit extends in a circumferential direction.

According to a third preferred aspect of the invention the inner barrel comprises means for guiding the plunger so as to allow it to be displaced in an axial direction only. The means for guiding the plunger may comprise pairs of ridges disposed at the inner wall of the inner barrel extending in a radial direction and spaced to receive an axially extending plunger flange or similar guide means between them. When its finger is disposed in the portion of the slit extending circumferentially, the plunger can however only be displaced in a radial direction, except after expelling the projection of the outer barrel from the slit. The circumferential portion of the slit is defined by a tongue. It is furthermore preferred for that tongue to comprise means for preventing rotation of the plunger upon expelling the projection of the outer barrel from the slit. The plunger is preferably made of a substantially stiff polymer material.

According to a fourth preferred aspect of the invention the inner and outer barrels comprise means for preventing their mutual rotation, such as one or several ridges at at least one of the outer wall of the inner barrel or the inner wall of the outer barrel and that are axially insertable in a corresponding number of slits in the outer of the wall of the outer barrel or the inner barrel, respectively, extending from the rear end of the slitted wall.

At their respective front ends the inner barrel and the outer barrel comprise axial channels disposed in line.

According to a fifth preferred aspect of the invention the hypodermic needle comprises, at its proximal end, means for interlocking with a holding portion disposed in the axial channel of the inner barrel. The means preferably comprise a saw-tooth profile, but another locking profile or a threaded profile is equally feasible. It is important that the interlocking means of the needle be easily insertable into the holding portion but that, once the needle is inserted, it cannot be easily withdrawn. The needle is mounted in the female portion of a conventional luer fitting which can be screwed on the male counterpart of the outer barrel. The needle is however mounted in a manner that allows it to be withdrawn from it in a proximal direction against a resistance which is substantially higher than the resistance required for inserting the end portion of the needle into the holding portion of the inner barrel.

Further advantages of the present invention will become evident from a study of a set of drawings illustrating a preferred embodiment of the invention which is described in detail, and from the appended claims.

DESCRIPTION OF THE DRAWINGS

For the sake of simplicity the sectional views do not show most of the elements disposed behind the plane of section.

DESCRIPTION OF A PREFERRED EMBODIMENT OF THE INVENTION

The preferred embodiment illustrated in the Figures comprises five parts: an outer barrel 1, an inner barrel 3, a plunger 5, and a luer fitting 7 provided with a hypodermic needle 9. They are essentially rotationally symmetrical; their axes coincide when mounted.

Figure 2:
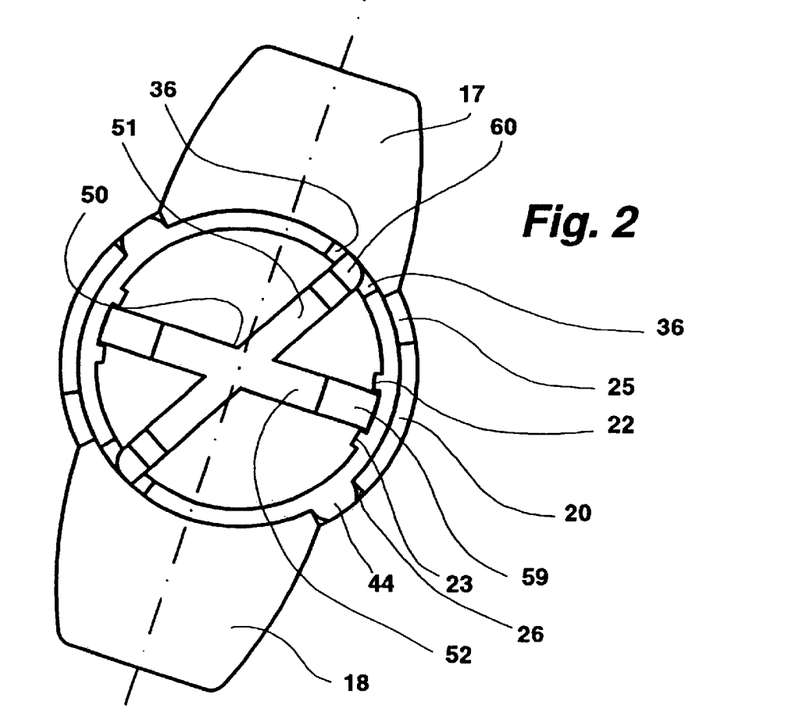
FIG. 2 is a top view of the syringe of FIG. 1, also indicating the plane of section S—S, with the plunger wings not shown.
Figure 3:
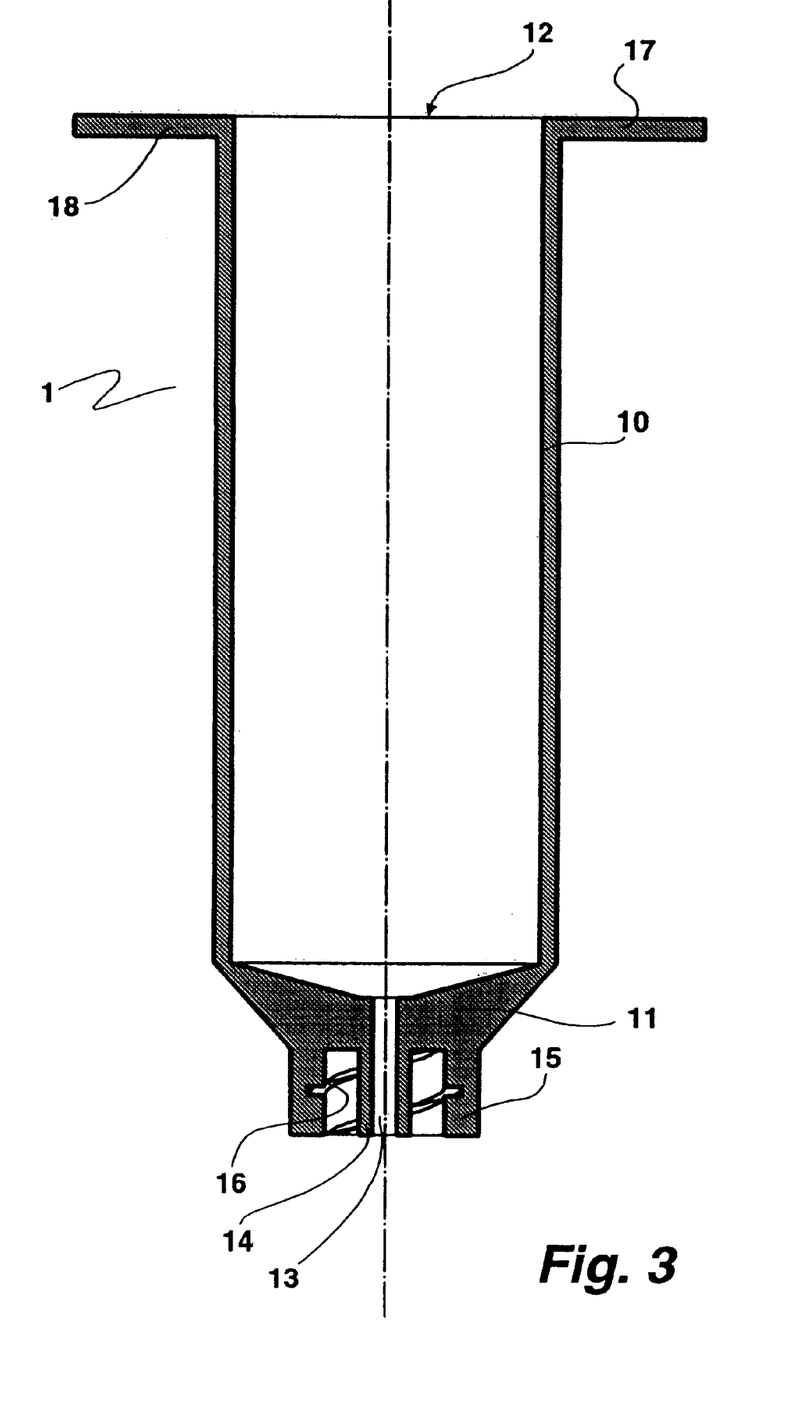
FIG. 3 is the outer barrel of the syringe of FIG. 1, in the same view.
Figure 4:
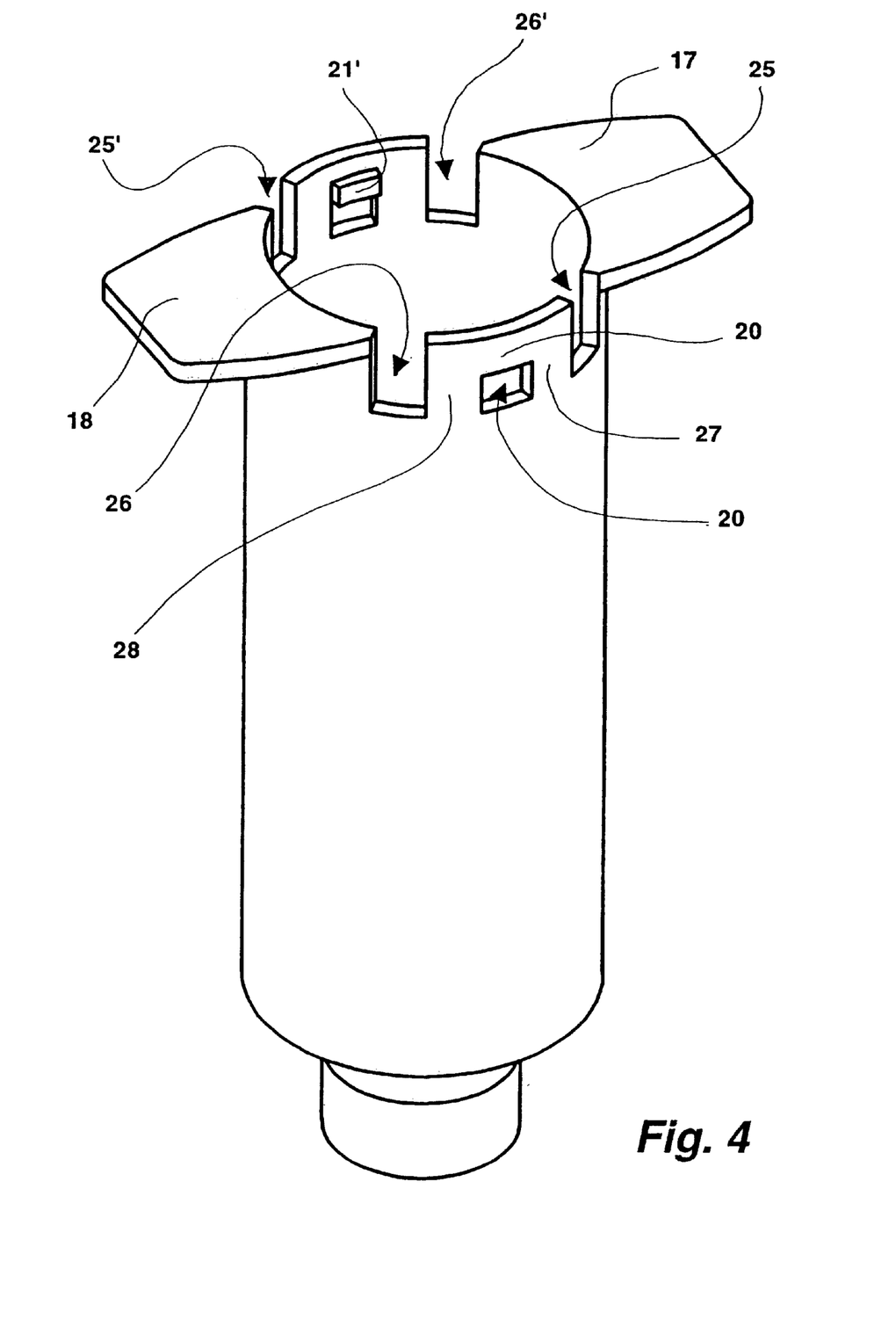
FIG. 4 is a side elevation view of the outer barrel of FIG. 3.

Referring to FIG. 3, at its bottom (front) end the outer barrel 1 has a nozzle 14 and a needle assembly mounting stud 15 provided with inner threads 16 and surrounding the nozzle 14 at a distance. The front wall 11 is considerably thicker than the outer barrel side wall 10. The inner and outer faces of the front wall 11 are conically narrowing in a distal direction but the central portion of the outer face is flat. The front wall 11 is penetrated by an axial channel 13. The edge 12 at its open rear end has radially extending holding wings 17,18. The following elements of the outer barrel are present in pairs. One set of elements suffices to make a functioning embodiment of the invention. The arrangement of the elements in balanced (mirrored) pairs, as disclosed in the present embodiment of the invention, is however superior. Pairs of elements are identified by same reference number X, X' of which only one (X) will be referred to, except for the drawings where reference is made to visible elements independent of designation (X or X'). Referring to FIGS. 2 and 4, the paired elements of the outer barrel 1 are: an axially extending slit 26 for receiving a cam 44 of the inner barrel; a base 20 from which a projection 21 extends radially inwards, ribs 27,28 supporting the base 20, separated by a cut-out 24 in the cylinder wall 10 and flanked by the slit 26 and a second slit 25 which does not receive a cam. The elements of the other pair are disposed in a mirrored position in respect of the barrel axis.

Figures 5, 5A, 6:
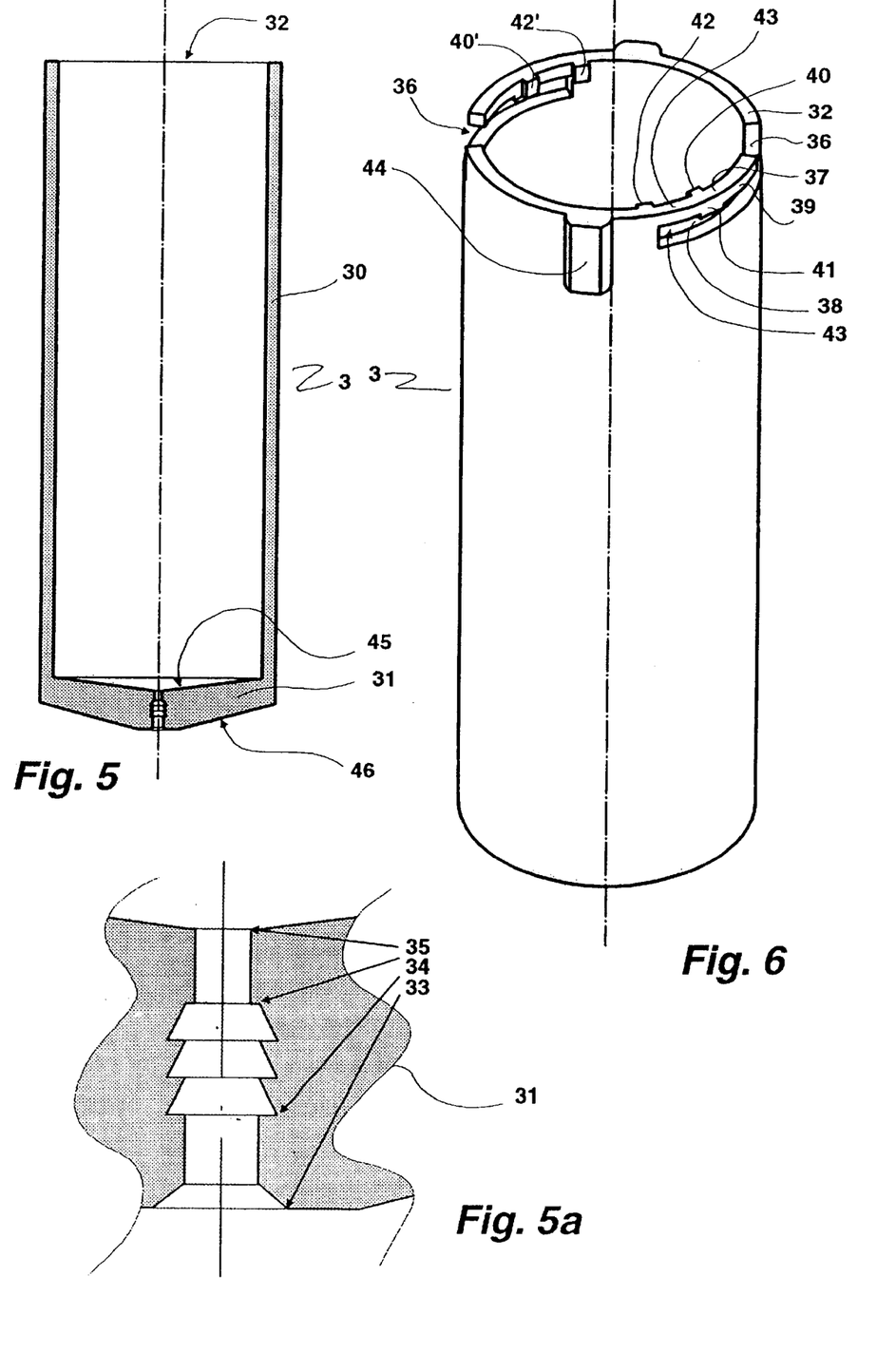
FIG. 5 is the inner barrel of the syringe of FIG. 1, in the same view.
FIG. 5a is an enlarged view of the needle insertion channel of the inner barrel of FIG. 5, in the same view.
FIG. 6 is a side elevation view of the inner barrel of FIG. 5.

Referring to FIG. 5, the inner barrel 3 fits snugly into the outer barrel 1 and comprises a cylinder wall 30 of about the same thickness as that of the outer barrel 1 and a considerably thicker front wall 31, the inner 45 and outer 46 faces of which are conically narrowing. Its open rear end edge is designated 32. Referring to FIG. 5a, the front wall 31 is penetrated by an axial channel comprising three portions: a frontal portion 33, an intermediate portion 34, and a rear portion 35. The frontal portion 33 has a diameter allowing the rear end anchoring portion 92 of the hypodermic needle 91 of FIGS. 9 and 10 to be easily inserted. The second portion 34 has a barbed (saw-tooth or similar) profile into which the rear end anchoring portion 92 with a matching profile can be inserted against a resistance and, once inserted, becomes locked against withdrawal. The third portion 35 is still more narrow so as to prevent further insertion of the needle anchoring portion 92.

Referring to FIG. 6, at its rear end circumferential edge 32, the inner barrel 3 has an L-formed slit delimitating a tongue 37. The slit extends from the rear edge 32 of the inner barrel 3 in a distal direction forming an axial slit section 36 from which the main slit portion 38 extends in a circumferential direction (clock-wise, when seen in a distal direction). The tongue 37 comprises a first section 39 extending from its free end, a wider second section 41 which narrows the width of the slit 38, and a third section 43 which defines an innermost portion of the slit that is wider again. Two plunger guide ridges 40,42 extending in an axial direction from the rear edge 32 are disposed on the inner wall of the inner barrel 3, with the first ridge 40 disposed on the second tongue section 41, and the second ridge 42 adjacent to the closed end of the slit 38.

Figures 7, 8:
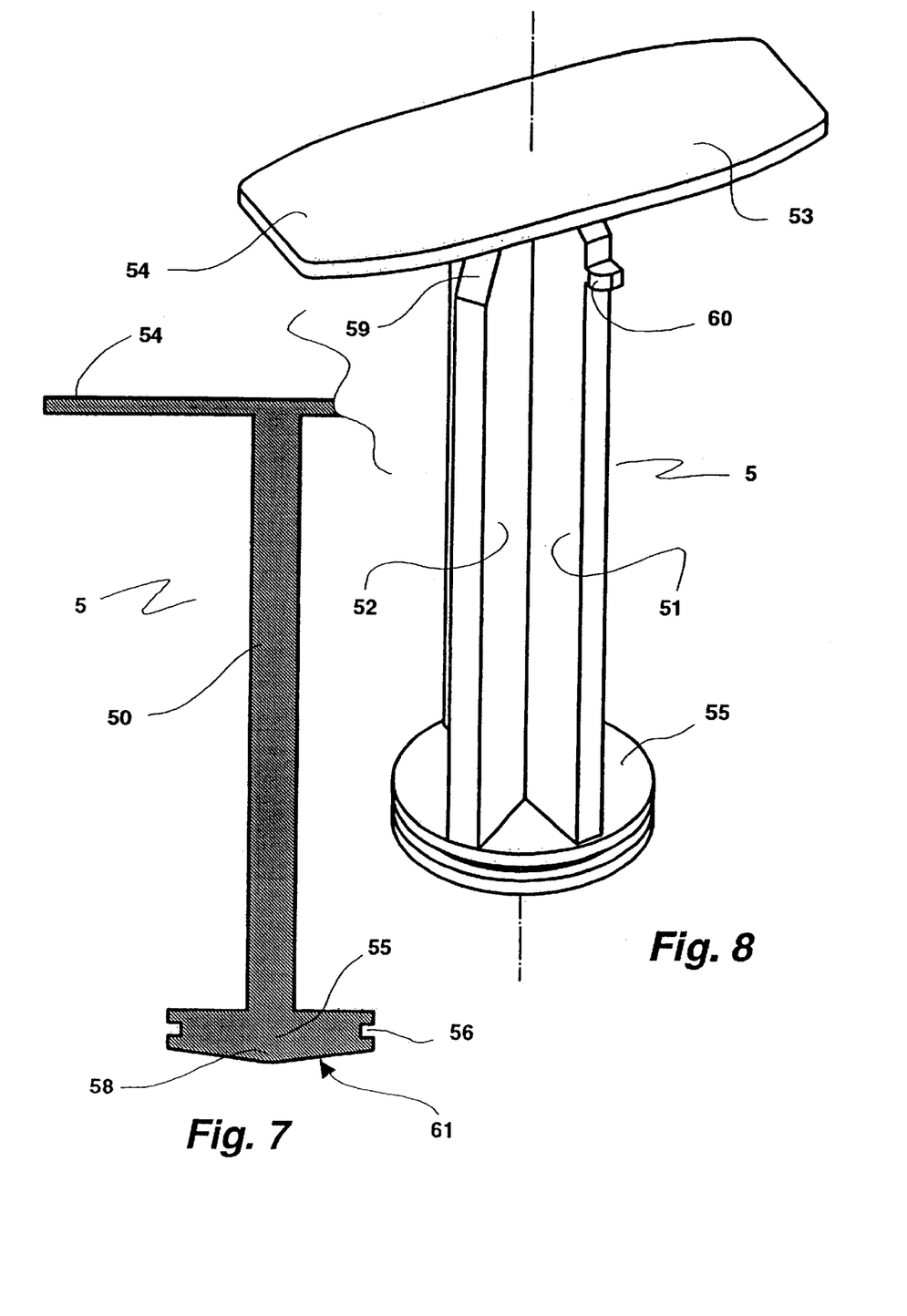
FIG. 7 is the plunger of the syringe of FIG. 1, in the same view.
FIG. 8 is a side elevation view of the plunger of FIG. 7.

Referring to FIGS. 2, 7 and 8, the plunger 5 comprises a shaft 50 with first 51 and second 52 flanges forming a skew cross in a radial section. Each of the flanges 51,52 has a generally rectangular profile. Wings 53,54 forming a plunger plate extend radially from the rear end of the plunger 5. The front portion of the plunger has the form of a cylinder 55 which narrows conically at its front portion 58. The front face 61 narrows by the same angle as the inner front wall face 45 of the inner barrel. The cylinder 55 has a peripheral groove 56 in which a flexible seal 57 is mounted (shown in FIG. 1).

The discussion concerns a condition in which the inner barrel 3 is fully inserted into the outer barrel 1, and the plunger 5 is fully inserted into the inner barrel 3. Disregarding the second flange 52 for a moment, the radial extension of the first flange 51 is short enough that it would allow unrestrained rotation of the plunger 3 except for a finger 60, which has a radial extension from the flange 51 that corresponds to about that of the outer cylinder face of the inner barrel 3. The radial extension of the second flange 52 corresponds to about the radius of the inner cylinder face of the inner barrel 3, except for a slanted portion 59 that extends from the plunger plate 53, 54 to beneath the distal end of the plunger guides 41,42. Disregarding the first flange 51 for a moment, if the plunger 3 is rotated, the slanted portion 59 of the second flange will abut against a corner face portion 47 of either of the guides 41,42 (as in FIG. 16 and particularly guide 41, due to clock-wise rotation). Because of the slightly flexible nature of the polymer material of the inner barrel 3, the resistance of the guides 41,42 against further rotation of the plunger 3 can be overcome by application of moderate force.

Figures 12, 16:
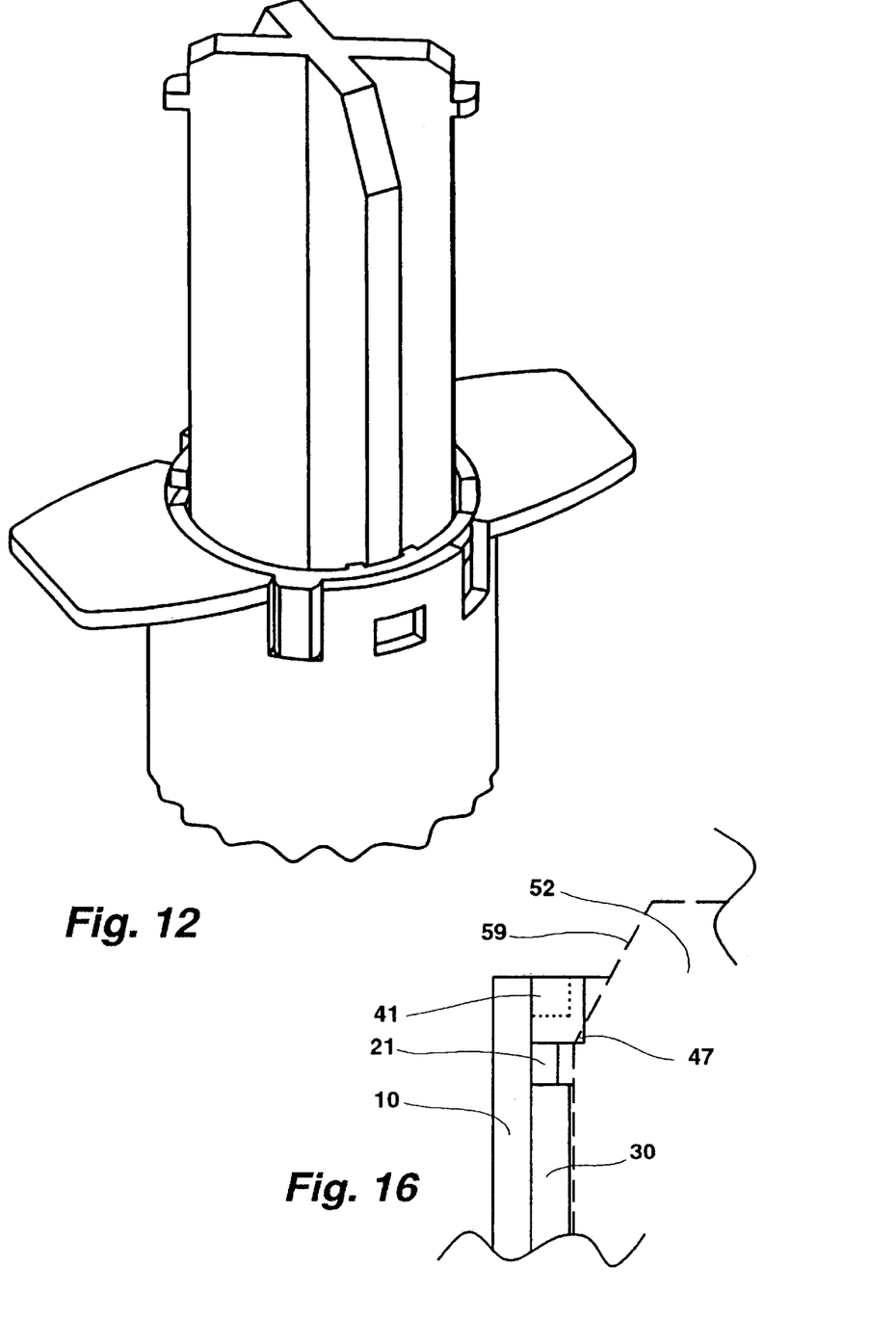
FIG. 12 is a side elevation view corresponding to FIG. 11, after filling the syringe with injection liquid.
FIG. 16 is a schematic side view illustrating the cooperation of the plunger guides of the inner barrel and the second shaft flange of the plunger.

If, however, the plunger 3 is drawn only slightly out from the inner barrel, each of the guides 41,42 will fully abut against the respective wall of the second flange 52 (depending on the direction of rotation) and resist further rotation of the plunger even if substantial force is applied or, if the second flange 52 is positioned between the guides 41,42, which are disposed at a suitable distance therefor, any rotation of the plunger 3 will be prevented.

Figure 9:
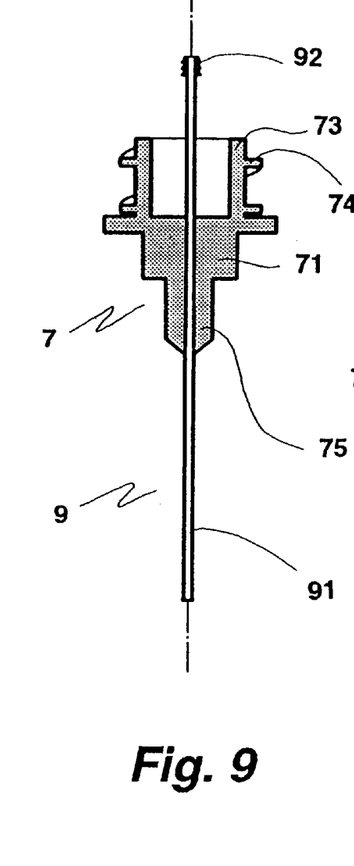
FIG. 9 is the luer fitting with a hypodermic needle of the syringe of FIG. 1, in the same view.
Figure 10:
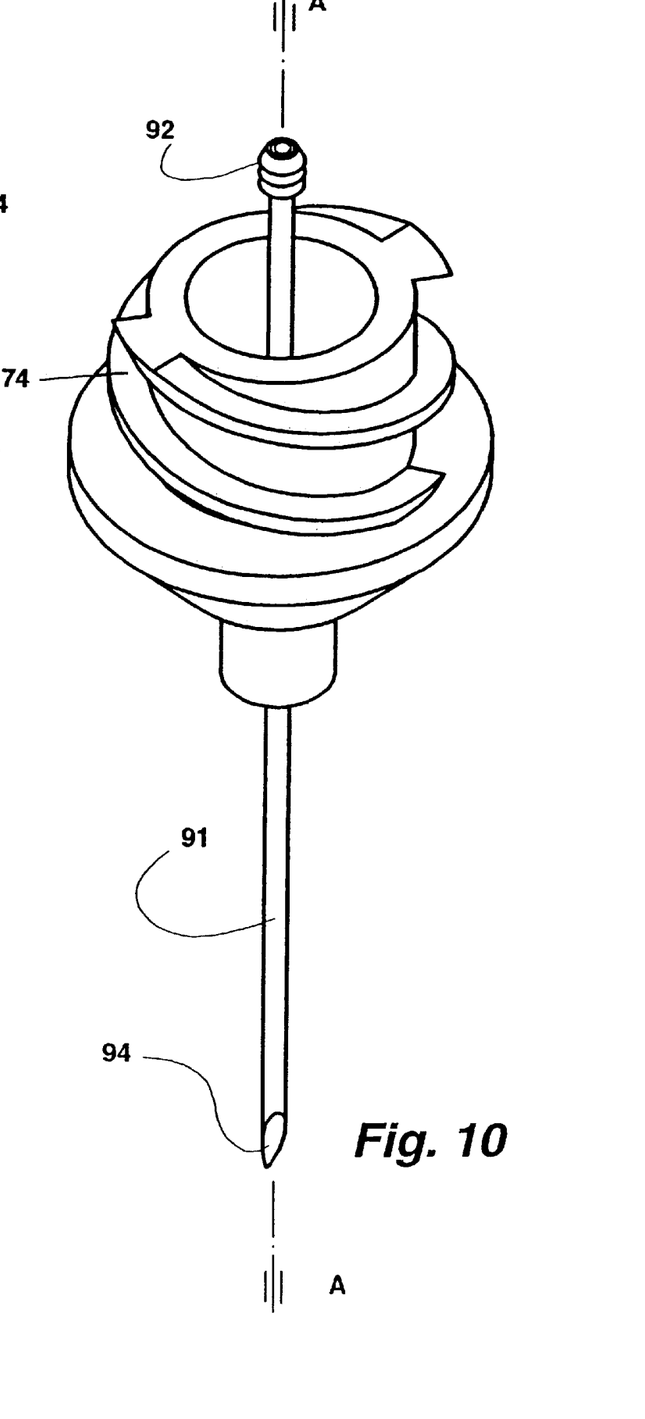
FIG. 10 is a side elevation view of the luer fitting and hypodermic needle of FIG. 9, enlarged.

Referring to FIGS. 9 and 10, the needle body 91 is tightly held in a central channel of the luer fitting 7 but can be displaced in that channel by applying a given force. At its proximal end the needle 9 is provided with the aforementioned anchoring portion 92 which has a barbed (saw-tooth) profile corresponding to that of the intermediate channel portion 41 of the inner barrel 3. The combination luer 7 fitting/needle 9 is mounted on the pre-mounted combination of outer barrel 1, inner barrel 3, and plunger 5 by inserting the proximal end of the needle 3 into the nozzle 14 and screwing the assembly on until sealing abutment is obtained. During this operation the anchoring portion 92 of the needle 9 becomes anchored in the intermediate channel portion 34 of the inner barrel front wall 31. The force required for anchoring the anchoring portion 92 in the intermediate channel portion 34 must be smaller than the force required to displace the needle 9 in respect of the luer fitting body 71. On the other hand, the force by which an already anchored needle 9 can be severed from the inner barrel 3 must be larger than said force required for displacement.

The operation of the syringe of the invention exemplified by the preferred embodiment described above is explained with reference to FIGS. 11–16. For reasons of clarity and simplicity the plunger plate 53,54 and, except for FIG. 15, the lower portion of the syringe have been omitted. The syringe may be provided to the user in either a pre-filled or an empty state. If it is provided pre-filled with an injectable fluid, the usual seal at the needle tip (not shown) will have to be removed before use. If it is provided empty, the syringe will have to be filled with an injectable fluid.

Figure 1:
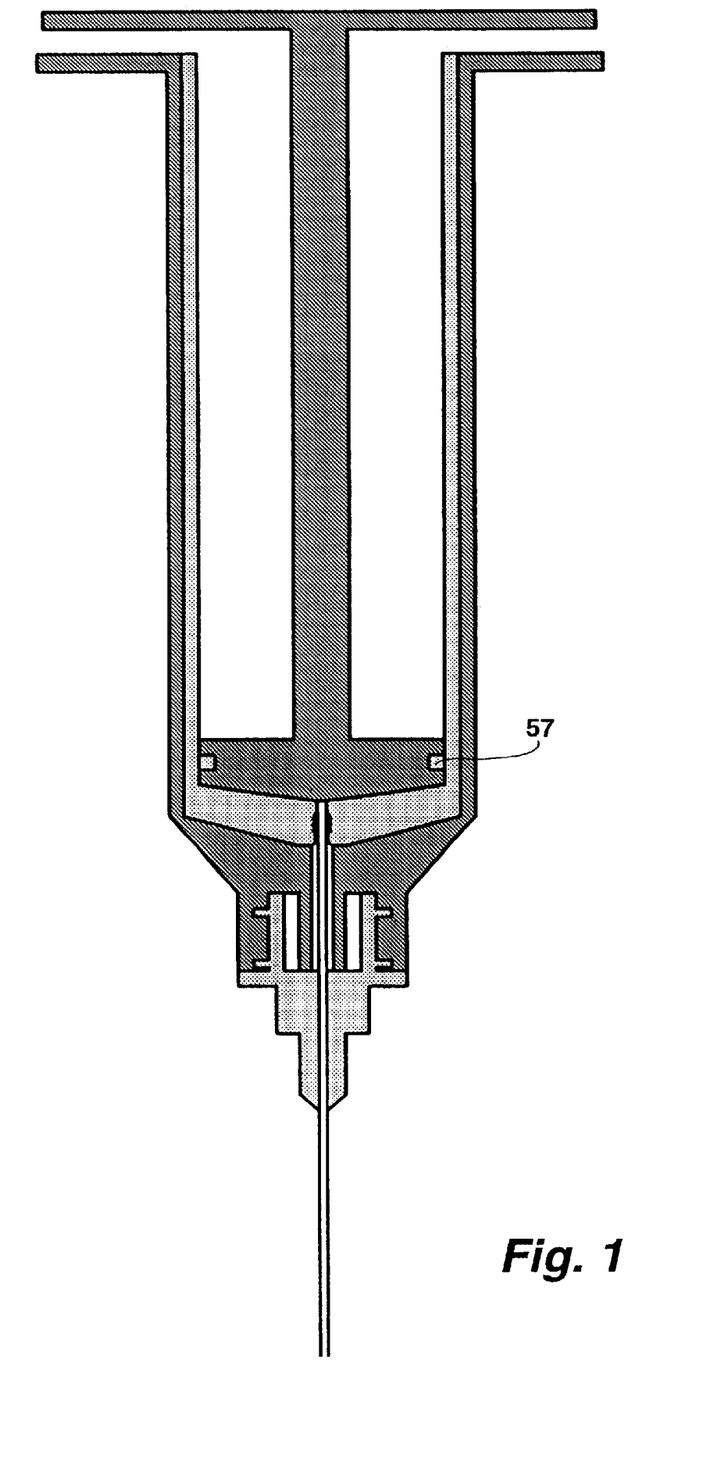
FIG. 1 is a sectional (S—S, FIG. 11) elevation view of a preferred embodiment of the disposable hypodermic syringe of the present invention.
Figure 1A:
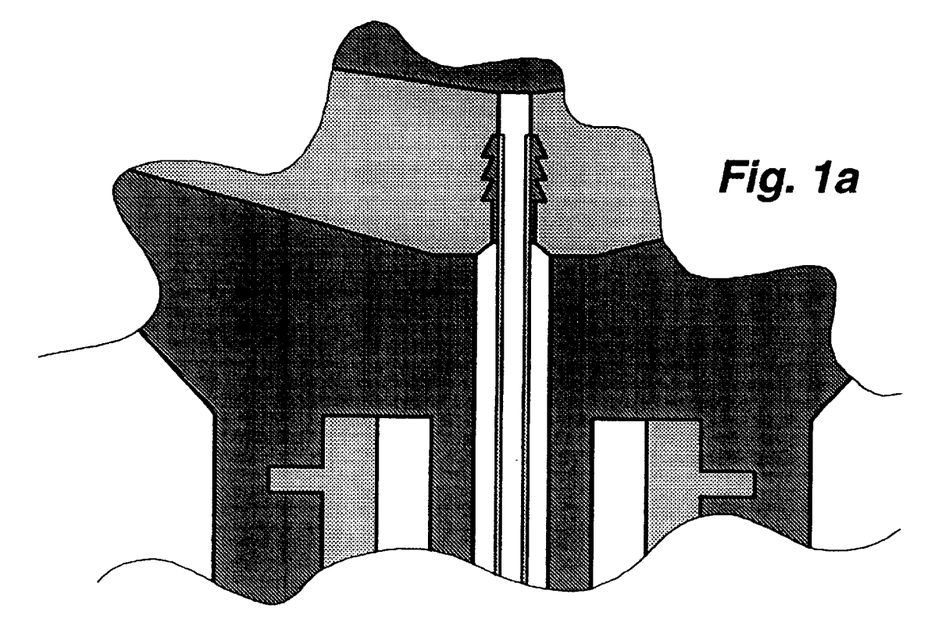
FIG. 1a is an enlarged view of a portion of FIG. 1.
Figures 11, 13, 14:
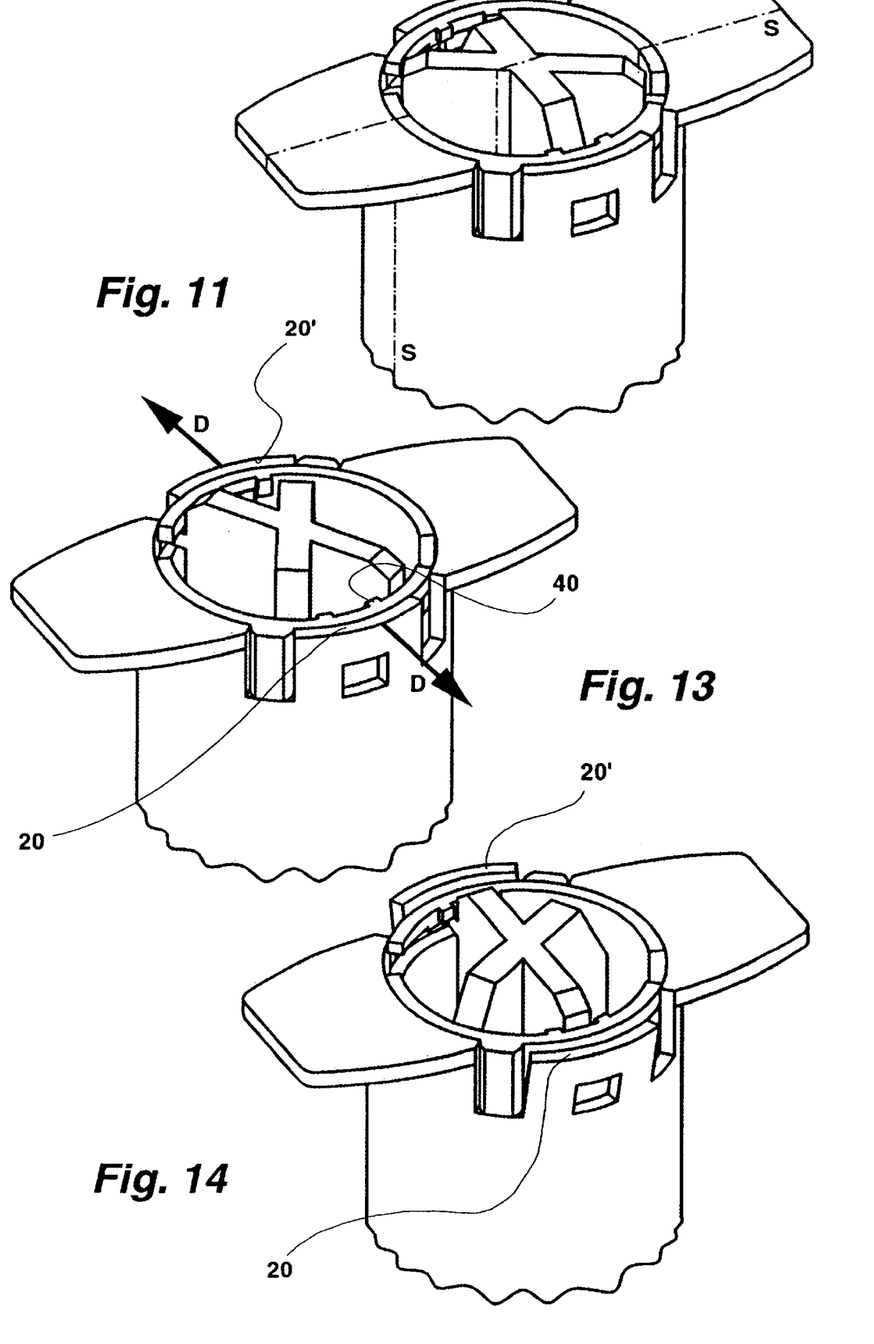
FIG. 11 is a side elevation view of the rear portion of the syringe of FIG. 1, prior to use and at the end of injection, the plunger wings not being shown for the sake of clarity.
FIG. 13 is a side elevation view corresponding to FIG. 11, with the plunger rotated so as to position the finger of the plunger flange about halfway in the circumferential slit of the inner barrel.
FIG. 14 is a side elevation view corresponding to FIG. 11, with the plunger further rotated sufficiently to make the plunger finger release the inner barrel from the outer barrel.

FIGS. 1, 2, and 11 illustrate an unfilled syringe according to the invention ready for use. It is important to notice how the individual parts of the syringe are mounted: the inner barrel 3 is mounted fully inserted in the outer barrel 1 with its cam 44 inserted in slit 26, whereby the inner barrel 3 and the outer barrel 1 become mutually locked against rotation. The plunger 5 is mounted in the inner barrel 3 fully inserted with its finger 60 into the axial portion 36 of slit 38. The inner barrel 3 and the plunger 5 are so matched that the first flange 51 of the plunger shaft 50 becomes located between the first 40 and second 42 plunger guides. Thus the plunger 5 can be withdrawn but not easily rotated due to the guides 40, 42.

By pulling the plunger 5 back the syringe is filled with the desired volume of injectable fluid. The relationship of the outer barrel 1, the inner barrel 3, and the plunger 5 at the end of the filling stage is shown in FIG. 12. A prefilled syringe of the invention would comprise the assembly outer barrel 1, inner barrel 3, and plunger 5 filled as shown in FIG. 12, in which the nozzle 14 is covered by a seal that has to be removed for mounting the luer fitting 7/needle 9 combination.

Upon injection the syringe returns to the state illustrated in FIG. 11. Now the operation of making the syringe unusable starts.

In the first step, the plunger 5 is rotated (clockwise) until the finger 60 abuts the second tongue section 40, whereby the width of the circumferential slit 38 where the tongue 60 has moved is narrowed so much as to provide some resistance against further rotation of the plunger 5. This situation is shown in FIG. 13. This resistance function is provided to let the medical person handing the syringe put it down temporarily if it is to be re-used for consecutive injections to the same patient.

Since the tongue 37 is somewhat flexible, the resistance against rotation of the plunger 3 offered by the second tongue section 40 is easily overcome. By rotating the plunger 5 further (clockwise) the finger 60 reaches the inner end of the slit 38 by which it is stopped. Simultaneously, the finger 60 expels the projection 21 of the outer barrel which had locked the inner barrel against withdrawal. The projection 21 can be pushed out from the slit portion formed by the tongue inner end section 43 due to the connection (by ribs 27,28) of the wall portion 20 carrying the projection 21 with the main portion of the outer barrel 3 being weakened by the cut-out wall portion 24 and the slits 25,26; the direction of displacement of the wall portions 20,20' is indicated by arrows D in FIG. 13. The situation with the inner barrel 3 thus released from the outer barrel 1 is shown in FIG. 14.

Figure 15:
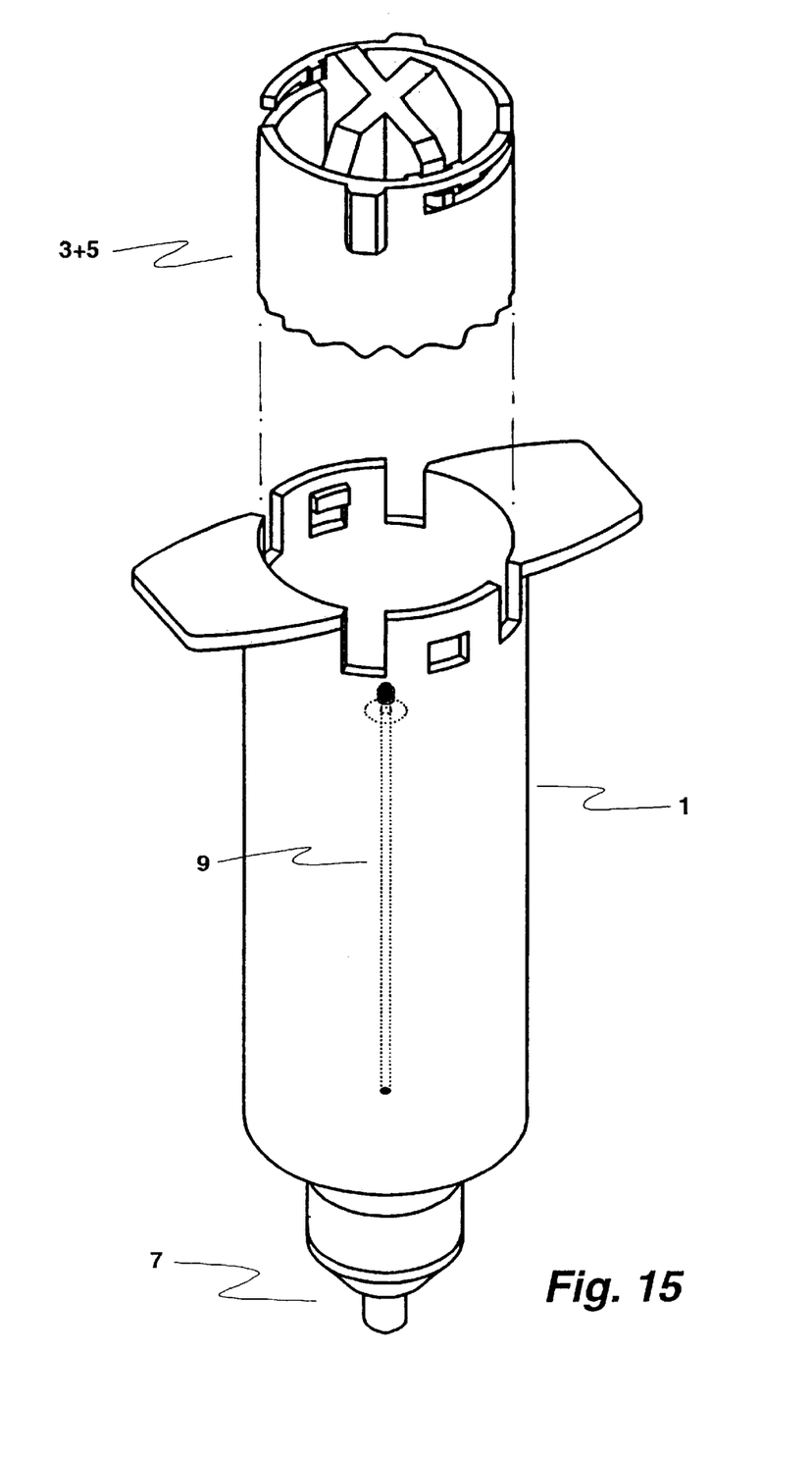
FIG. 15 is a slightly reduced side elevation view corresponding to FIG. 11, after withdrawing the inner barrel with the needle so as to position the needle in the space between the outer barrel and the inner barrel.

Now the inner barrel 3 can be withdrawn by pulling the plunger 5 back. Since the needle 9 is firmly fixed to the inner barrel 3, it moves with it until it is becomes housed in the space formed between the outer barrel 1 and the inner barrel 3 (FIG. 15). Further withdrawal of the combination inner barrel 3/plunger 5/needle 9 is hindered by the upper face of the conical plunger end portion 58 abutting the projection 20.

If desired, the plunger 5 with the inner barrel 3 can be pushed back into the outer barrel 1. Making the axial channel of the inner barrel slightly deviate from the outer barrel 1 axis will displace the needle point 94 after withdrawal from the outer barrel axial channel 13 so as to make re-insertion impossible. Instead, when pushing the plunger/inner barrel/needle combination back into the outer barrel the point 94 will hit the inner front wall face of it. Because of its substantial thickness, the front wall 11 offers sufficient resistance against penetration so that the needle 9 will be permanently bent, and may even break.

Although the present invention has been described in relation to a particular embodiment thereof, many other variations and modifications and other uses will become apparent to those skilled in the art. It is preferred, therefore, that the present invention be limited to not by the specific disclosure herein, but only by the appended claims.

What is claimed is:

1. A disposable hypodermic syringe, comprising:

an outer barrel defined by a first surrounding wall and also having a first front end wall and a first open rear end;

an inner barrel defined by a second surrounding wall and also having a second front end wall and a second open rear end, the barrel being slidingly disposable in the outer barrel with the second front end wall at the first front end wall;

a hypodermic needle disposed axially and located at the first front end wall of the outer barrel so as to penetrate the first front end wall, the needle having a rear end, which is held by the front end wall of the inner barrel;

a plunger slidingly disposable in the inner barrel;

first interlocking elements at the outer barrel and the inner barrel for interlocking the outer barrel with the inner barrel when the inner barrel is in a fully inserted position in the outer barrel, a releasing element on the plunger for releasing the inner barrel from the outer barrel while also interlocking the plunger with the inner barrel to allow the plunger and the inner barrel to be withdrawn in combination with the hypodermic needle with the inner barrel being withdrawn from the outer barrel for a distance sufficient to displace the needle into a space formed inside the outer barrel and between the outer barrel and the withdrawn inner barrel.

2. The syringe of claim 1, wherein the outer barrel first surrounding wall includes an inner wall around the inner barrel; the first interlocking elements for locking the inner barrel to the outer barrel comprise a circumferential slit in the second surrounding wall of the inner barrel disposed near the second rear end and a projection extending in a radial direction inwardly from the inner wall of the outer barrel so as to be located in the slit.

3. The syringe of claim 2, wherein the first surrounding wall of the outer barrel includes a wall section of the outer barrel flanked by axially extending, circumferentially separated slits and the projection is disposed at the inner barrel.

4. The syringe of claim 2, wherein there is a cutout in the wall of outer barrel, and the projection is disposed proximally of the cut-out.

5. The syringe of claim 2, wherein the plunger includes a radial flange and the releasing element of the plunger for releasing the inner barrel from the outer barrel comprises a finger extending radially from the radial flange of the plunger, the finger being insertable into the slit of the inner barrel and being displaceable along the slit to a position to expel the projection of the outer barrel from the slit.

6. The syringe of claim 5, wherein the slit includes one open end for insertion of the plunger finger.

7. The syringe of claim 6, wherein the slit is shaped so that the finger is inserted in the slit by a distal displacement of the plunger.

8. The syringe of claim 2, where the slit comprises an insertion portion extending in an axial direction joined by a remainder of the slit which extends in a circumferential direction.

9. The syringe of claim 1, wherein the inner barrel comprises guide elements for guiding the plunger for allowing the plunger to be displaced in an axial direction only.

10. The syringe of claim 9, wherein the inner barrel second surrounding wall includes an inner wall; the guide elements for guiding the plunger comprise pairs of ridges disposed at the inner wall of the inner barrel, extending inward in a radial direction and being circumferentially spaced apart to receive an axially extending plunger guide element between them.

11. The syringe of claim 9, wherein the plunger is only displaceable in a radial direction when the finger is disposed in the circumferentially extending portion of a slit, except after the finger expels the projection of the outer barrel from the slit.

12. The syringe of claim 9, wherein the circumferentially extending portion of a slit of the inner barrel defines a tongue which prevents rotation of the plunger after expelling of the projection of the outer barrel from the slit.

13. The syringe of claim 1, further comprising rotation preventing elements acting between the inner barrel and the outer barrel for preventing their mutual rotation.

14. The syringe of claim 13, wherein the outer barrel first surrounding wall includes an inner wall, and the inner barrel second surrounding wall includes an outer wall; and the rotation preventing elements comprise at least one ridge disposed at at least one of the outer wall of the inner barrel and the inner wall of the outer barrel and corresponding slits in the wall of the outer of outer barrel and the inner barrel, respectively, wherein the slits extend from the rear end of the respective wall, wherein the ridges are axially insertable in the respective corresponding slits.

15. The syringe of claim 1, wherein the hypodermic needle has a proximal end; the inner barrel having an axial channel near the proximal end, a holding portion disposed in the axial channel of the inner barrel, interlock elements of the needle interlocking with the holding portion.

16. The syringe of claim 15, wherein the interlock elements comprise a saw-tooth profile or a threaded profile.

17. The syringe of claim 15, wherein the interlock elements of the needle are shaped to be easily insertable into the holding portion but, once inserted, not to be easily withdrawn.

18. The syringe of claim 17, wherein the hypodermic needle is mounted in a luer fitting in a manner to allow the needle to be withdrawn from the fitting in a proximal direction against a resistance which is substantially higher than the resistance required for inserting the end portion of the needle into the holding portion of the inner barrel.

* * * * *